United States Patent [19]

Ingle

[11] Patent Number: 4,458,518

[45] Date of Patent: Jul. 10, 1984

[54] APPARATUS AND METHOD FOR CALIBRATING A PHOTOPLETHYSMOGRAPH

[75] Inventor: Frank W. Ingle, Palo Alto, Calif.

[73] Assignee: Medasonics, Inc., Mountain View, Calif.

[21] Appl. No.: 394,637

[22] Filed: Jul. 1, 1982

[51] Int. Cl.³ .................. A61B 5/02; G01D 18/00
[52] U.S. Cl. ........................................ 73/1 R; 128/688
[58] Field of Search .................. 73/1 R; 128/688; 356/243; 73/3, 1 H

[56] References Cited

U.S. PATENT DOCUMENTS

| | | | |
|---|---|---|---|
| 2,241,190 | 5/1941 | Fenning | 128/688 |
| 4,164,937 | 8/1979 | Spencer | 128/688 X |
| 4,355,903 | 10/1982 | Sandercock | 356/243 X |

FOREIGN PATENT DOCUMENTS 2249667  4/1973  Fed. Rep. of Germany ...... 128/688

Primary Examiner—S. Clement Swisher
Assistant Examiner—Tom Noland
Attorney, Agent, or Firm—Warren M. Becker

[57] ABSTRACT

An apparatus for calibrating a photoplethysmograph system comprising a white card mounted in the cone of a speaker. The card is mounted a predetermined distance from a photoplethysmograph sensor for providing an output from the sensor corresponding to the DC or venous mode. An oscillation is provided for oscillating the white card at a frequency corresponding to the average heartbeat for producing on the output of the sensor a signal corresponding to an average heartbeat. By adjusting the gain of the photoplethysmograph apparatus to obtain a constant amplitude output from the system, a calibration signal is obtained.

8 Claims, 6 Drawing Figures

APPARATUS AND METHOD FOR CALIBRATING A PHOTOPLETHYSMOGRAPH

The present invention relates to a photoplethysmograph (PPG) in general and in particular to an apparatus and method for calibrating a photoplethysmograph.

BACKGROUND OF THE INVENTION

A photoplethysmograph is an apparatus for diagnosing venous incompetence in the extremities, the presence of arterial supply, and the obstruction of the carotid arteries. It is extremely sensitive to the relative amount of blood in a capillary bed and to arterial pulsation.

In general, a photoplethysmograph comprises a probe coupled to an adjustable gain AC and DC amplifier. The outputs of the amplifiers are coupled to a chart recorder for displaying signals detected by the probe.

In the probe there is provided a light source and a photosensor. Typically the light source comprises a light-emitting diode (LED). An LED is used since it produces light in a narrow spectral band and has a low power dissipation. Low power dissipation is essential since any heating of the skin against which the LED is placed produces a vasoactive response which will cause an erroneous measurement. The wave length of the radiation from the LED is typically in the range of 800–950 nanometers.

The photosensor may be a photocell, phototransistor or photodiode which is provided with an infrared filter to reduce its sensitivity to ambient light. A resistive sensor could also be used; however, it is considered to be inferior because its speed of response depends on ambient light level and is too slow to allow visualization of the dichrotic notch that is present in arterial pulsations. In addition, the sensitivity of a resistive sensor depends exponentially on the light level. In contrast, phototransistors and photodiodes are both quite linear and have a rapid response and are sensitive to the near-infrared.

In many cases, the diagnosis and treatment of medical conditions require numerous tests which extend over a long period of time. In such cases the diagnostician is frequently looking for relatively small changes in the medical condition. In order to do this, it is important that the medical instrumentation used by the diagnostician be accurate and repeatable—that is, nothing should change in the instrumentation between uses thereof which impairs the measurement of or otherwise masks small changes in a patient's medical condition which may have occurred since the last test. Alternatively, where changes in the medical instrumentation do occur, a means must be provided for calibrating such instrumentation to compensate for those changes.

In photoplethysmographic apparatus, changes in the instrumentation which can impair the measurement of small changes in medical condition from test to test or otherwise mask such changes are manifold. For example, in any given instrument, there may be, between tests, changes in the LED current used for driving the LED, a change in the LED brightness, a change in the phototransistor sensitivity, a change in the gain of the AC and DC amplifiers in the photoplethysmograph apparatus, gradual changes in the optics—such as face plate scratches or surface contamination of the sensing units—a change in the gain of a chart recorder, or changes in the frequency response of the photoplethysmograph amplifiers. Some of the above changes may be due to aging of the apparatus. Others may be due to ambient temperature. Still others may be due to changes in the output of the power supply used in the apparatus. Moreover, the output of the apparatus may change when changing sensor modules, the amplifiers, or the chart recorders in any given system.

Heretofore, so far as is known, there has been no suitable means proposed for calibrating an otherwise conventional photoplethysmograph apparatus to compensate for the above described changes.

SUMMARY OF THE INVENTION

In view of the foregoing, a principal object of the present invention is an apparatus and method for calibrating a photoplethysmograph apparatus.

Another object of the present invention is a method and apparatus for calibrating a photoplethysmograph apparatus to compensate for changes in LED current and brightness, photoplethysmograph sensitivity and amplifier and chart recorder gain.

Another object of the present invention is an apparatus and method for compensating for or measuring changes in the frequency response of the above described circuit elements.

Still another object of the present invention is an apparatus and method for calibrating a photoplethysmograph apparatus in which sensor modules or probes or any other component thereof have been changed.

In a preferred embodiment of the present invention there is provided a white, non-specular planar reflector, such as a card, mounted to the cone of a speaker. The speaker and card assembly are mounted in a housing with an oscillator for driving the speaker. On an exterior surface, the housing is further provided with a sensor-receiving receptacle for holding a photoplethysmograph sensor a predetermined distance from the card. The distance, typically 12.5 mm, provides an output on a chart recorder which corresponds to the typical output obtained when the sensor is attached to the ball of a finger on a hand which is held at heart level. With the sensor held the predetermined distance from the white card, the oscillator moves the speaker at a frequency of 2 Hz. The frequency of 2 Hz roughly corresponds to an average heartbeat of 72 beats per minute. With the speaker oscillating the white card, the gain of the photoplethysmograph amplifiers are adjusted for providing, on the output of the chart recorder, a signal of predetermined amplitude -e.g., 50 mm.

By calibrating the photoplethysmograph apparatus in the manner described to obtain on the output of the chart recorder a signal having said predetermined amplitude before each use thereof, the operator thereof can be assured that any changes from previous tests in the output of the chart recorder will be due to changes in the medical condition of the patient being tested and not due to changes in the photoplethysmograph apparatus being used.

BRIEF DESCRIPTION OF THE DRAWING

The above and other objects, features and advantages of the present invention will become apparent to those skilled in the art from the following detailed description of the accompanying drawings, in which.

DETAILED DESCRIPTION OF THE INVENTION

Figure 1:
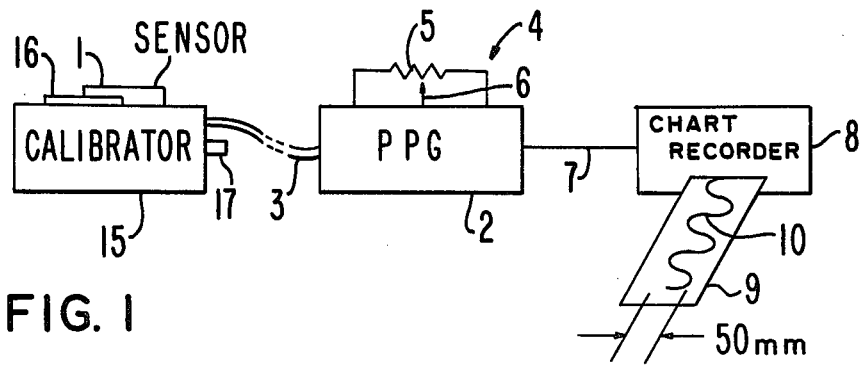
FIG. 1 is a block diagram of a photoplethysmograph apparatus with a calibrating apparatus according to the present invention.

Referring to FIG. 1, there is provided a sensor 1. Sensor 1 is coupled to a photoplethysmograph amplifying apparatus 2 by means of a cable 3. The photoplethysmograph (PPG) apparatus 2 is provided with a variable gain control 4 represented by a resistor 5 and an adjustable contact 6. The PPG 2 is coupled by means of a cable 7 to a chart recorder 8. The chart recorder 8 outputs on chart paper 9 a signal 10 corresponding to the output of the sensor 1. The amplitude of the signal 10 is controlled by the gain adjustment control 4 in the PPG 2.

In accordance with the present invention, there is provided a calibrating apparatus 15. The apparatus 15 is provided with a sensor-receiving receptacle 16 and a control switch 17.

Figure 2:
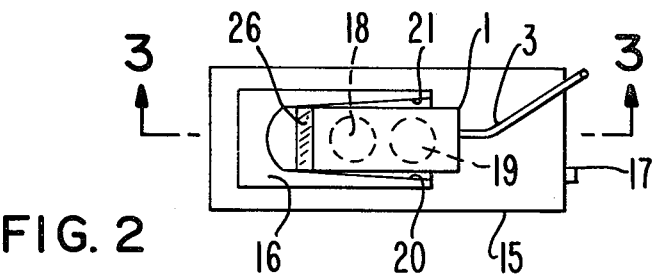
FIG. 2 is a top view of a calibrating apparatus according to the present invention.
Figure 3:
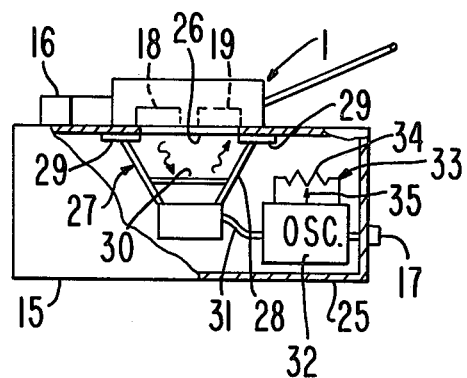
FIG. 3 is a partial cross-sectional view taken along lines 3—3 of FIG. 2.

Referring to FIGS. 2 and 3, the sensor 1, which is a conventional photoplethysmograph sensor, is provided with a light-emitting diode (LED) 18 and a photodetector 19. The wave length of the radiation emitted from the LED 18 is typically in the range of 800–900 nanometers. The photodetector or photosensor 19 is a phototransistor typically fitted with an infrared filter to reduce its sensitivity to ambient light. In addition to its wave length, the LED 18 should also be chosen to have low power dissipation to prevent undesirable heating of the skin against which the LED is placed. This is necessary to minimize any vasoactive response due to heat, which will cause an erroneous measurement.

The sensor receptacle 16 is provided with a pair of interior side walls 20 and 21. Side walls 20 and 21 converge slightly toward the left end of the receptacle 16 so as to provide a snug fit for holding the sensor 1 during calibration of the photoplethysmograph apparatus.

In the calibrating apparatus 15 there is provided a housing 25. The sensor receptacle 16 is mounted to the top of the housing 25. At the base of the receptacle 16 and mounted across an opening provided therefor in the housing 25, there is provided a transparent plate 26. Plate 26 is transparent to the radiation emitted by the LED 18. Inside the housing 25 there is provided a speaker 27. Speaker 27 is provided with a cone 28 having a diameter of approximately two inches. The upper edge of the cone 28 is mounted to the interior of the housing 25 by any suitable means, such as screws (not shown), with one or more removable shims 29 located between the upper edge of the cone 28 of the speaker 27 and the interior of the housing 25. The cone 28 of the speaker 27 is centered relative to the transparent window 26. Mounted in the interior of the cone 28 there is provided a white non-specular planar reflector 30. Typically reflector 30 comprises a white card having a characteristic 90 percent reflectivity and is commercially available from Eastman Kodak of Rochester, New York. The card 30 may be mounted to the cone 28 by any suitable means such as glue or epoxy. The shims 29 are provided for adjusting the average distance between the sensor 1 and the card 30 to a predetermined distance as hereinafter described.

Coupled to the voice coil of the speaker 27 by means of a line 31, there is coupled the output of an oscillator 32. Oscillator 32 is provided with an adjustable gain control 33, represented by a resistor 34 and a movable contact 35. The control switch 17 is provided for activating the oscillator 32.

Figure 4:
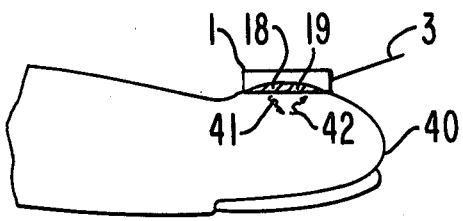
FIG. 4 is a partially broken-away view of a sensor in contact with the ball of a finger (digit).

Referring to FIG. 4, the sensor 1 is mounted, as by double-sided cellophane tape, to the ball of a finger 40. With the sensor mounted to the ball of a finger 40, the LED 18 emits radiation of a predetermined wave length, typically in the range of 800–950 nanometers. The emitted radiation indicated by the wavy arrow 41 is directed into the finger 40. Some of the radiation is absorbed by the blood in the finger and some is reflected by the tissue in the finger. The reflected radiation is represented by the wavy line 42. The amount of radiation which is absorbed and reflected depends on the amount of blood in the capillary bed. The radiation 42 which is reflected from the tissue is detected by the photosensor 19. The output of the photosensor 19 is amplified in the photoplethysmograph amplifying circuit 2 and displayed on the output of the chart recorder 8.

Figure 5:
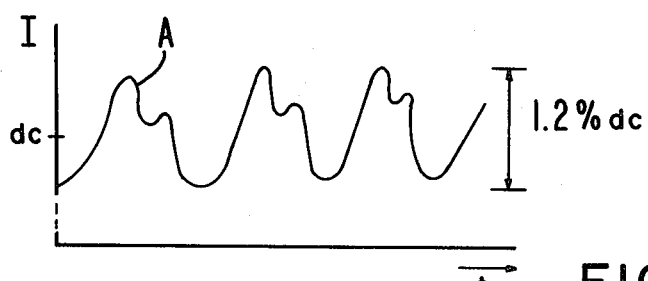
FIG. 5 is a representation of the AC pulsatile signal obtained on the output of the chart recorder of FIG. 1 during a conventional diagnostic test.

Referring to FIG. 5, there is shown a representation of the current output (I) of the photosensor 19 vs. time (T). The output is represented by the curve designated A. The curve A corresponds to the arterial blood flow in the finger 40 and has a frequency corresponding to the pulse, typically in the range of 40–240 beats per minute or $\frac{2}{3}$ Hz to 6 Hz. A convenient simulation of curve A is a frequency of 2 Hz or 120 beats per minute. The signal of FIG. 5 has both an AC component and a DC component. The DC component corresponds to an average amount of blood in the capillary bed of the finger 40. Tests have shown that the AC component is a relatively small fraction of the DC component—e.g., 1.2 percent of the DC component.

Figure 6:
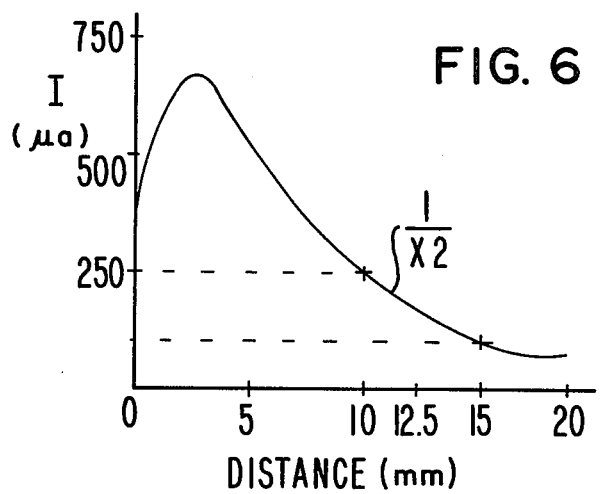
FIG. 6 is a curve representing the output of a typical phototransistor as a function of distance between the phototransistor and the card in the calibrating apparatus according to the present invention.

Referring to FIG. 6, there is shown a plot made by varying the spacing between the white, non-specular planar reflector 30 and the sensor 1. The current output from the photosensor 19 was recorded as a function of distance. Beyond 9 mm the curve is found to correspond well to the expected $1/x^2$ response. When the sensor 1 is attached to the ball of the index finger as shown in FIG. 4, and the hand is held at heart level, the PPG phototransistor DC current is 130–230 microamperes. This corresponds to the magnitude of the signal reflected from the white card 30 at a distance of 10.6–15.4 mm. For this reason, the white card 30 in the calibrator 15 is mounted such that the predetermined average distance between the phototransistor 19 and the white card 30, when the sensor 1 is placed in the receptacle 16, is approximately 12.5 mm.

With an AC signal which is only 1.2 percent of the size of the DC venous mode signal, it can be seen from the slope of the curve of FIG. 6 that the variation in position required at the 12.5 mm spacing is only 12.8 micrometers. To generate a corresponding signal in the calibrator 15, the oscillator 32 is adjusted to provide a sinosoidal current to the speaker 27 of 78 milliamperes peak to peak at a frequency of 1 Hz.

With a sinosoidal current of 78 milliamperes peak to peak at frequency of 2 Hz, the gain control circuit 4 of the PPG amplifier circuit 2 is adjusted to provide an output on the chart recorder 8 of a constant amplitude—e.g., 50 mm.

By calibrating the photoplethysmograph in the manner described, such that the output of the chart recorder is a predetermined amplitude prior to each use of the photoplethysmograph apparatus, it will be appreciated that, regardless of any changes in the photoplethysmograph apparatus, the operators thereof can be assured that any deviation from the predetermined amplitude of the calibration signal during actual use will represent an accurate measure of changes in the physical condition of the capillary bed being investigated.

While a preferred embodiment of the present invention is disclosed and described, it is contemplated that those skilled in the art may make various changes and modifications to the apparatus and the operation thereof without departing from the spirit and scope of the present invention. For these reasons, it is intended that the scope of the invention not be limited to the embodiment described but be determined by reference to the claims hereinafter provided and their equivalents.

What is claimed is:

1. Apparatus for calibrating a photoplethysmograph system, said system having a sensor, including a source of radiation and means for detecting said radiation; means for amplifying an output from said detecting means; and means for displaying an output of said amplifying means; comprising:
   means having a reflecting surface for reflecting radiation from said source to said detecting means;
   means for supporting said source and detecting means at a predetermined average distance from said reflecting surface;
   means for moving said reflecting surface toward and away from said source and detecting means at a predetermined frequency; and
   means for adjusting the gain of said amplifying means to display on said displaying means a signal having said predetermined frequency and a predetermined amplitude.

2. An apparatus according to claim 1 wherein said supporting means comprises:
   a housing;
   a receiving means mounted to the top of said housing for receiving said sensor; and
   an opening in said housing for transmitting radiation from said source to said reflecting surface and radiation reflected therefrom to said detecting means.

3. An apparatus according to claim 1 wherein said supporting means comprises means for adjusting said predetermined average distance between said source and detecting means and said reflecting surface.

4. Apparatus for calibrating a photoplethysmograph system, said system having a sensor, including a source of radiation and means for detecting said radiation; means for amplifying an output from said detecting means; and means for displaying an output of said amplifying means; comprising:
   reflecting means including a non-specular planar reflecting surface for reflecting radiation from said source to said detecting means;
   means for supporting said source and detecting means at a predetermined average distance from said reflecting surface;
   a speaker having a speaker cone and a voice coil;
   means for mounting said reflecting means to said speaker cone;
   means coupled to said voice coil for moving said speaker cone and said reflecting surface of said reflecting means mounted thereto relative to said source and detecting means at a predetermined frequency; and
   means for adjusting the gain of said amplifying means to display on said displaying means a signal having said predetermined frequency and a predetermined amplitude.

5. An apparatus according to claim 4 wherein said moving means comprises means for adjusting the amplitude of the movement of said speaker cone at said predetermined frequency.

6. An apparatus according to claim 4 wherein said reflecting means comprises a white card, a said speaker cone comprises speaker cone have a diameter of approximately 2-inches and said mounting means comprises means for cementing the peripheral edges of said card to said cone.

7. A method of calibrating a photoplethysmograph system, said system having having a sensor, including a source of radiation and means for detecting said radiation; means for amplifying an output from said detecting means; and means for displaying an output of said amplifying means; comprising the steps of:
   reflecting light from said source from a reflecting surface to said detecting means;
   moving said reflecting surface toward and away from said source and detecting means at a predetermined frequency; and
   adjusting the gain of said amplifying means to display on said displaying means a signal having said predetermined frequency and a predetermined amplitude.

8. A method according to claim 7 wherein said step of moving said reflecting surface comprises the steps of:
   mounting said reflecting surface to the cone of a speaker; and
   oscillating said cone at said predetermined frequency.

* * * * *